United States Patent
Leasure

(10) Patent No.: US 7,172,551 B2
(45) Date of Patent: Feb. 6, 2007

(54) CYCLICAL PRESSURE CORONARY ASSIST PUMP

(75) Inventor: Bryan Leasure, Austin, TX (US)

(73) Assignee: Scimed Life Systems, Inc., Maple Grove, MN (US)

( * ) Notice: Subject to any disclaimer, the term of this patent is extended or adjusted under 35 U.S.C. 154(b) by 125 days.

(21) Appl. No.: 10/822,315

(22) Filed: Apr. 12, 2004

(65) Prior Publication Data

US 2005/0228211 A1   Oct. 13, 2005

(51) Int. Cl.
*A61M 1/10*    (2006.01)

(52) U.S. Cl. .................. 600/16; 600/17; 623/3.11; 623/3.16; 623/3.17

(58) Field of Classification Search ............ 600/16–18; 623/3.1, 3.11, 3.16, 3.17; 606/191, 197, 606/1; 135/15.1–48
See application file for complete search history.

(56) References Cited

U.S. PATENT DOCUMENTS

| | | | |
|---|---|---|---|
| 3,860,968 A * | 1/1975 | Shapiro .................... 623/3.22 |
| 4,175,264 A | 11/1979 | Schiff |
| 4,522,195 A * | 6/1985 | Schiff ......................... 600/18 |
| 4,771,765 A * | 9/1988 | Choy et al. ................. 600/18 |
| 4,957,504 A | 9/1990 | Chardack |
| 5,176,619 A * | 1/1993 | Segalowitz ................. 600/18 |
| 5,250,167 A * | 10/1993 | Adolf et al. ................ 310/309 |
| 5,337,754 A * | 8/1994 | Heaven et al. .............. 600/562 |
| 5,352,180 A | 10/1994 | Candelon et al. |
| 5,360,445 A | 11/1994 | Goldowsky |
| 5,389,222 A * | 2/1995 | Shahinpoor ................. 310/309 |
| 5,397,349 A * | 3/1995 | Kolff et al. .................. 623/3.3 |
| 5,578,012 A | 11/1996 | Kamen et al. |
| 5,613,935 A | 3/1997 | Jarvik |
| 5,725,004 A * | 3/1998 | Moulder ..................... 135/20.2 |
| 5,827,171 A * | 10/1998 | Dobak et al. ................. 600/16 |
| 5,865,721 A | 2/1999 | Andrews et al. |
| 5,910,124 A * | 6/1999 | Rubin ......................... 601/153 |
| 5,928,132 A * | 7/1999 | Leschinsky .................. 600/16 |
| 5,941,813 A * | 8/1999 | Sievers et al. ................ 600/16 |
| 6,053,932 A * | 4/2000 | Daniel et al. ............... 606/200 |
| 6,074,365 A | 6/2000 | Hähndel et al. |
| 6,079,430 A * | 6/2000 | Yamamoto ................... 135/16 |
| 6,084,321 A | 7/2000 | Hunter et al. |
| 6,136,025 A * | 10/2000 | Barbut et al. ................ 623/3.1 |
| 6,149,578 A | 11/2000 | Downey et al. |
| 6,165,119 A * | 12/2000 | Schweich et al. ............. 600/16 |
| 6,210,318 B1 * | 4/2001 | Lederman ..................... 600/18 |

(Continued)

FOREIGN PATENT DOCUMENTS

EP   0 567 788 A1   11/1998

(Continued)

*Primary Examiner*—Robert E. Pezzuto
*Assistant Examiner*—Tammie K. Heller
(74) *Attorney, Agent, or Firm*—Crompton, Seager & Tufte LLC

(57) ABSTRACT

An intravascular pump, which may be a left ventricle assist device, comprising a wall defining a pumping chamber, the wall support by struts, the struts attached to or part of an actuation system to move the wall from an expanded position to a contracted position and back to operated the pump, the actuation system may be electrically activated shape memory alloy struts, electroactive polymeric struts, or may be a balloon, struts attached to a slidable member or other suitable system.

20 Claims, 9 Drawing Sheets

U.S. PATENT DOCUMENTS

| | | | |
|---|---|---|---|
| 6,228,018 B1 * | 5/2001 | Downey et al. | 600/18 |
| 6,245,007 B1 | 6/2001 | Bedingham et al. | |
| 6,249,076 B1 * | 6/2001 | Madden et al. | 310/363 |
| 6,264,601 B1 * | 7/2001 | Jassawalla et al. | 600/16 |
| 6,299,575 B1 | 10/2001 | Bolling | |
| 6,376,971 B1 * | 4/2002 | Pelrine et al. | 310/363 |
| 6,387,037 B1 | 5/2002 | Bolling et al. | |
| 6,390,969 B1 | 5/2002 | Bolling et al. | |
| 6,406,422 B1 | 6/2002 | Landesberg | |
| 6,428,464 B1 | 8/2002 | Bolling | |
| 6,464,655 B1 | 10/2002 | Shahinpoor | |
| 6,468,200 B1 * | 10/2002 | Fischi | 600/18 |
| 6,530,876 B1 | 3/2003 | Spence | |
| 6,533,716 B1 * | 3/2003 | Schmitz-Rode et al. | 600/16 |
| 6,545,384 B1 * | 4/2003 | Pelrine et al. | 310/309 |
| 6,579,223 B2 * | 6/2003 | Palmer | 600/16 |
| 6,610,004 B2 | 8/2003 | Viole et al. | |
| 6,638,253 B2 * | 10/2003 | Breznock | 604/164.04 |
| 6,638,294 B1 * | 10/2003 | Palmer | 606/200 |
| 6,676,692 B2 * | 1/2004 | Rabkin et al. | 623/1.11 |
| 6,685,621 B2 | 2/2004 | Bolling et al. | |
| 6,793,618 B2 * | 9/2004 | Schweich et al. | 600/37 |
| 6,893,431 B2 * | 5/2005 | Naimark et al. | 604/891.1 |
| 2004/0249408 A1 * | 12/2004 | Murphy et al. | 606/198 |

FOREIGN PATENT DOCUMENTS

WO     WO 98/18508     5/1998

* cited by examiner

CYCLICAL PRESSURE CORONARY ASSIST PUMP

FIELD

The present invention generally relates to coronary assist pumps. More specifically, the present invention relates to coronary assist pumps implantable within the heart.

BACKGROUND

Millions of Americans are afflicted with heart failure, which is an inability of the heart to pump enough blood to sustain normal bodily functions. Every year, 15,000 to 20,000 of these patients require heart transplants but only a small fraction of these patients receive a transplant. Those patients who eventually receive a heart transplant wait about 200 days in the hospital. During this time in the hospital, the patient will need enhanced heart pumping function to keep them alive. Left ventricle assist devices (LVADs) have been helpful in this application, which is called "bridge to transplant". Moreover, some are developing LVADs that may be permanently installed and eliminate the need for a heart transplant.

One current LVAD is a pump that bypasses the left ventricle. The pump is installed in the upper abdomen and pumps blood from the left ventricle through a first tube and into the aorta through a second tube. This device requires major surgery to install and requires 24 hour monitoring once it is installed.

Another type of LVAD is a tiny turbine that is installed into the left ventricle chamber.

Some side effects of current LVADs include aortic valve stenosis, thrombosis formation, and right heart failure. The constant pumping pressure that some of the LVADs generate, rather than the systolic/ diastolic cycle associated with a healthy heart, may cause some of this valve and right heart damage. Also, the right heart may not have the strength to push the blood through the mitral valve into the left ventricle because of the high pressures some of the LVADs generate.

SUMMARY

One example embodiment pertains to an intravascular pump that may be installed into the left ventricle of the heart as a left ventricle assist device. The pump may include a flexible wall defining a pumping chamber and a pumping mechanism. The pumping mechanism may include a frame attached to the wall and an actuation mechanism attached to the frame. One possible actuation mechanism is an umbrella-like mechanism including a central shaft and struts slideably attached between the shaft and the frame. The struts may be actuated by use of a shape memory alloy, balloon, electroactive polymer, or wire, as described in more detail below. The pump may include a power source, a controller, and sensors.

Another example embodiment is a method of installation. The pump is loaded into a percutaneous catheter such as a guide catheter. The catheter is then introduced into the vasculature of a patient and advanced to the left ventricle of the heart. The pump may then be advanced from the guide catheter or the catheter may be withdrawn from around the pump.

The above summary of some example embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

Figure 1:
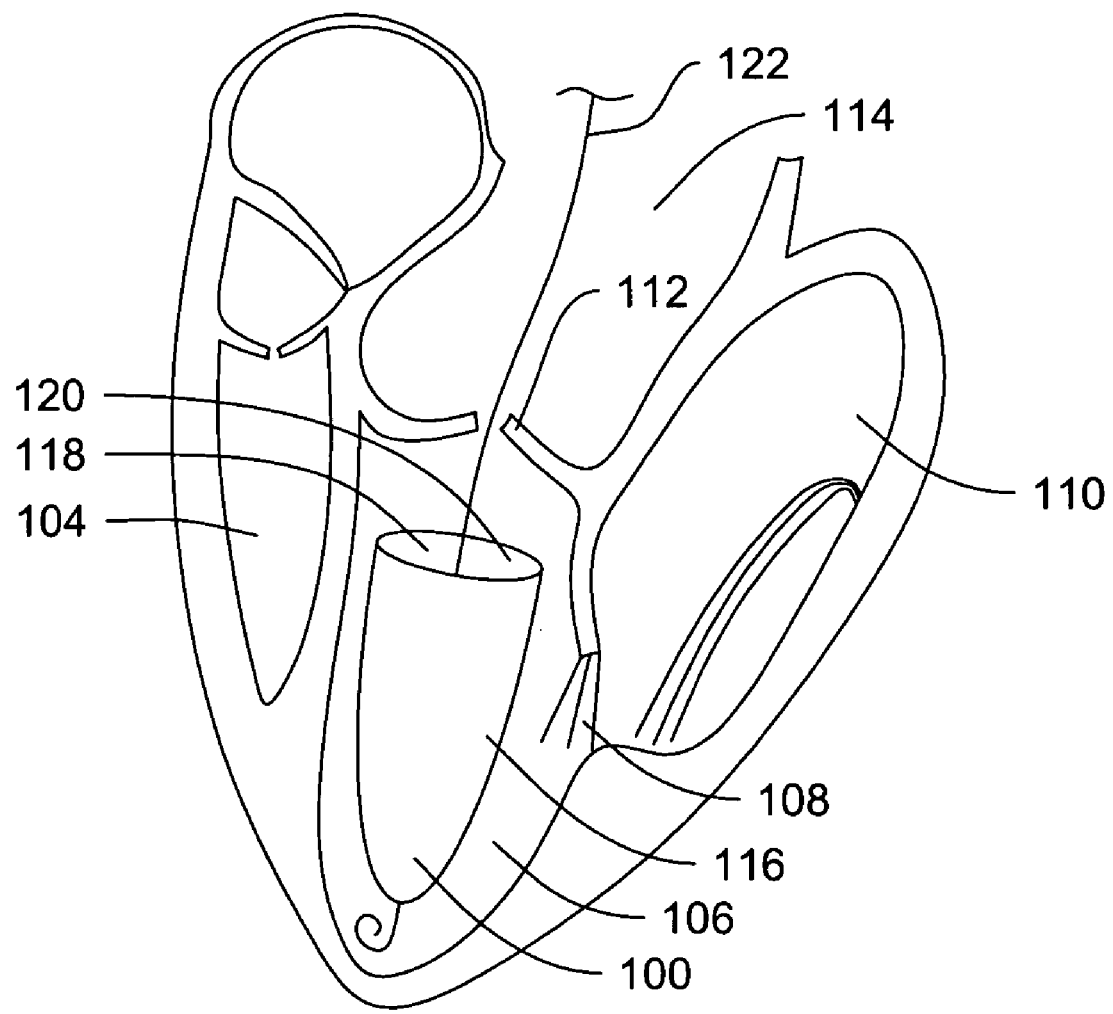
FIG. 1 depicts a cross-sectional view of a heart with a side diagrammatic view of a pump 100 disposed therein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF EXAMPLE EMBODIMENTS

As used in this specification and the appended claims, the singular forms "a", "an", and "the" may include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a diagrammatic side cross-sectional view of a heart 102 with a side view of a pump 100 disposed therein. Heart 102 includes right ventricle 104, left ventricle 106, mitral valve 108, left atrium 110, and aortic valve 112. The view also shows a portion of the aorta 114. Pump 100 is disposed in left ventricle 106. Blood is pumped by the left atrium 110 through mitral valve 108 and into left ventricle 106. The left ventricle then pumps the blood through the aortic valve into general circulation in the body. Pump 100 is positioned to aid the function of left ventricle 106 and consequently is positioned so that the outtake is facing aortic valve 112. Pump 100 has a wall 116 that defines a pumping chamber 118. Pumping chamber 118 has an opening 120, which may serve as both an intake and outtake for pump 100. Pump 100 has a generally conical shape to better fit in left ventricle 106. Pump 100 may have a round or a slightly oval cross-section, as desired for a particular application. Wall 116 may be made of any biocompatible flexible material. Wall 116 may be made from a non-elastic material, or from an elastic material. If wall 116 is made from an elastic material, the wall may be sized to be stretched when the pump is in an expanded position. Pump 100 may include elongate member 122. Elongate member 122 may include a shaped tip 123 such as a curl to position pump 100 in the desired location and to prevent trauma to the ventricle wall. Pump 100 operates by moving wall 116 between an expanded state and a contracted state, preferably synchronous with the left ventricle's operation.

Figure 2:
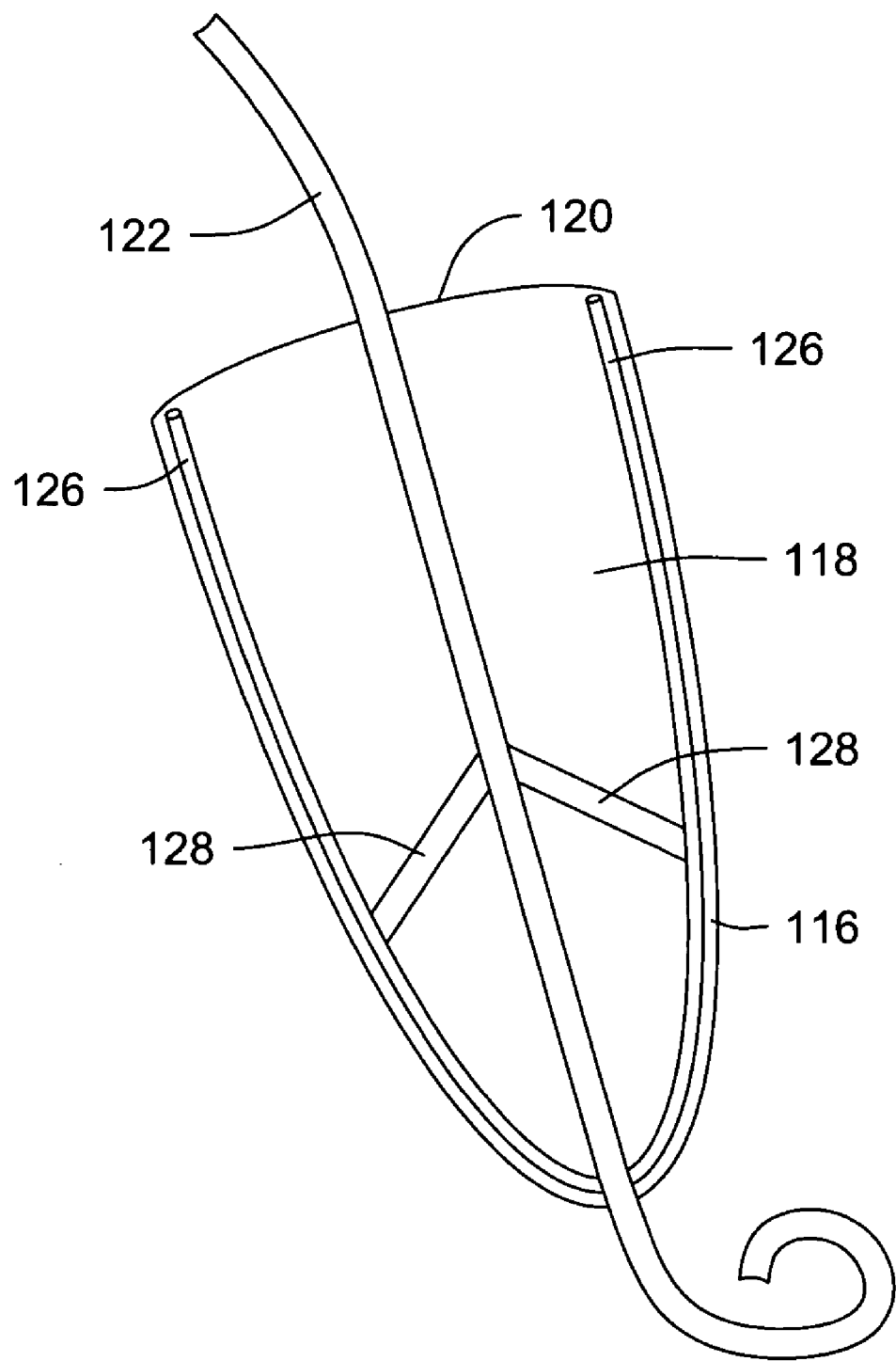
FIG. 2 depicts a diagrammatic cross-sectional view of pump 100 in an expanded position.

FIG. 2 is a plan cross-sectional view of pump 100. Pump 100 includes wall 116 defining cavity 180. The cavity has an opening 120 at a first end. A pumping mechanism 124 includes frame 126 and actuating struts 128. Frame 126 includes support struts 130. Support struts 130 are attached to wall 116 and should be relatively rigid. Actuating struts 128 are made from a shape memory material. There may be any suitable number of support struts and actuating struts, and the number of support struts should generally correspond to the number of actuating struts. For example, there may be 3, 4, 5, 6, 7 or 8 of support struts and a corresponding number of actuating struts.

Shape memory materials include NiTi alloys such as Nitinol™ and other alloys such as CuAlNi. Shape memory materials may be plastically deformed in their martensitic phase to a first shape and then when heated to their austenitic phase may assume another shape. When cooled down back to the martensitic phase, they may return to the first shape. Many shape memory alloys, including Nitinol™, may be heated to their austenitic phase by passing a current through them.

In this embodiment, actuating struts 128 are made from a suitable shape memory alloy. Each strut may have two electrically separated branches connected at the end to form an electrical path out and back. Each strut may also electrically connected to a voltage source through elongate member 122 or through another suitable source. Each strut may be formed so that the pump is in its contracted position when the shape memory material is in the austenitic phase and in its expanded position when the shape memory alloy is in its martensitic phase. Alternatively, the struts could be formed so that each strut is in the austenitic phase when the pump is in its expanded position and in the martensitic phase when the pump is in its contracted position. In another alternative, the actuating struts could be divided into two equal or roughly equal groups, each group electrically connected to a separate voltage source, or to a voltage source that could apply voltage to each group selectively. The first group is formed as the struts in the first embodiment described above, and the second group is formed as the struts in the second embodiment describe above. In this manner, some of the actuating struts could be working during both the expansion and contraction of the pump. Each of the struts would have a suitable polymeric coating to both thermally and electrically isolate the struts from the body fluid and to prevent electical shorts, and the electrical conduits in elongate member 122 would be suitably insulated.

In an alternative configuration, each strut may include only a single electrical path. The voltage may flow through elongate member 122, through each actuating strut 128, through each connecting support strut 126, and back to a separate electrical conduit in elongate member 122. Of course, in this configuration, struts 126 would be suitably insulated as well.

Figure 3:
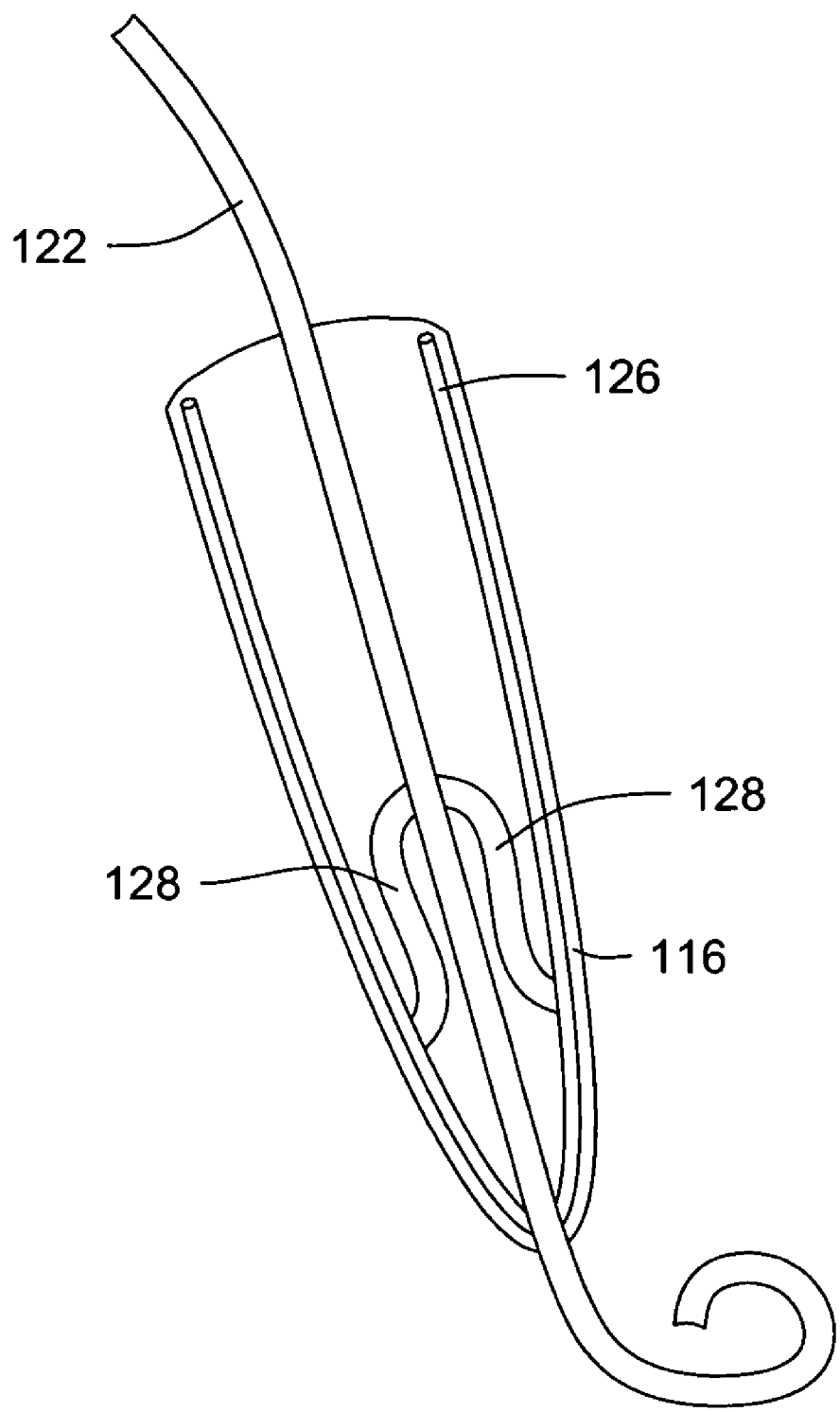
FIG. 3 depicts a diagrammatic cross-sectional view of pump 100 in a contracted position.

FIG. 3 is a diagrammatic cross-sectional view of pump 100 in the contracted position. In operation, intermittent voltage from the voltage source moves actuating struts 128 into the martensitic phase by heating the struts up. When the voltage ceases, actuating struts 128 cool down to their austenitic phase. Pump 100 therefore may be moved between an expanded state and a contract state, as illustrated by FIGS. 1 and 2 respectively. When the pump moves to the expanded state, blood fills cavity 118. When the pump moves to the contracted state, blood rushes out in the direction of the aortic valve (see FIG. 1), and thus enhances the operation of the left ventricle.

Figure 4:
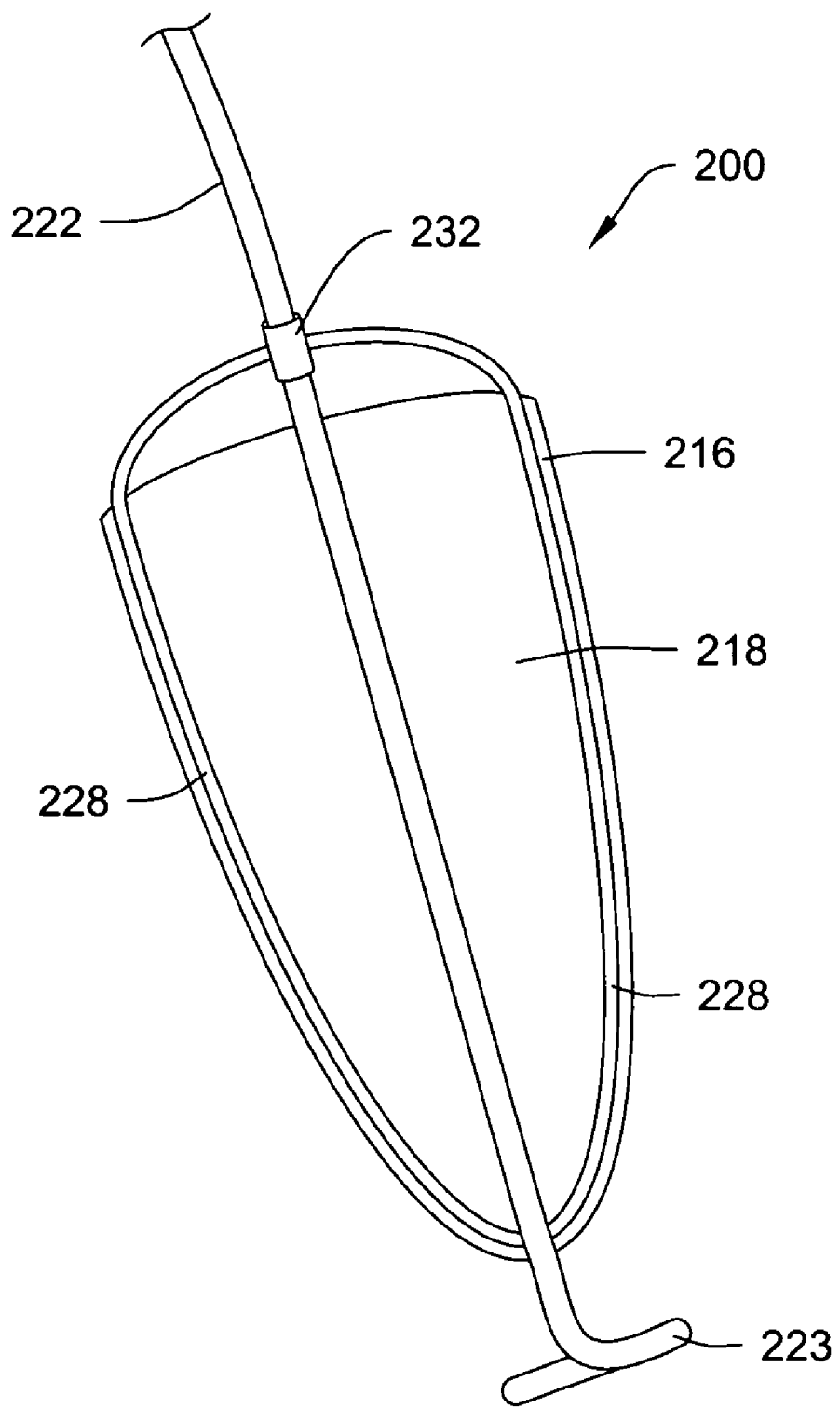
FIG. 4 depicts a diagrammatic cross-sectional view of a pump 200 in an expanded position.

FIG. 4 is a diagrammatic cross-sectional view of a pump 200. Pump 200 includes wall 216, which forms pumping cavity 218 having opening 220. An elongate member 222 passes through the center of pumping cavity 218 and may include atraumatic end 223, which may be a flexible coil or other suitable configuration. The actuation mechanism consists of actuating struts 228. Actuating struts 228 are attached to wall 216 generally along the length of the wall and are attached to sliding collar 232 at a first end and to elongate member 222 at a second end. Actuating struts 228 are made from a shape memory alloy such as Nitinol™ as described above. Each strut has two separate sections electrically connected at sliding collar 232. Each section of each strut is also electrically connected to a voltage source at elongate member 222 at the second end. Thus voltage may travel down elongate member, up through each strut, back down each strut and back up the elongate member. Each strut also has a polymeric layer surrounding the shape memory material to provide electrical and thermal insulation. There may be any suitable number of actuating struts. For example, there may be 3, 4, 5, 6, 7, or 8 actuating struts.

Figure 5A:
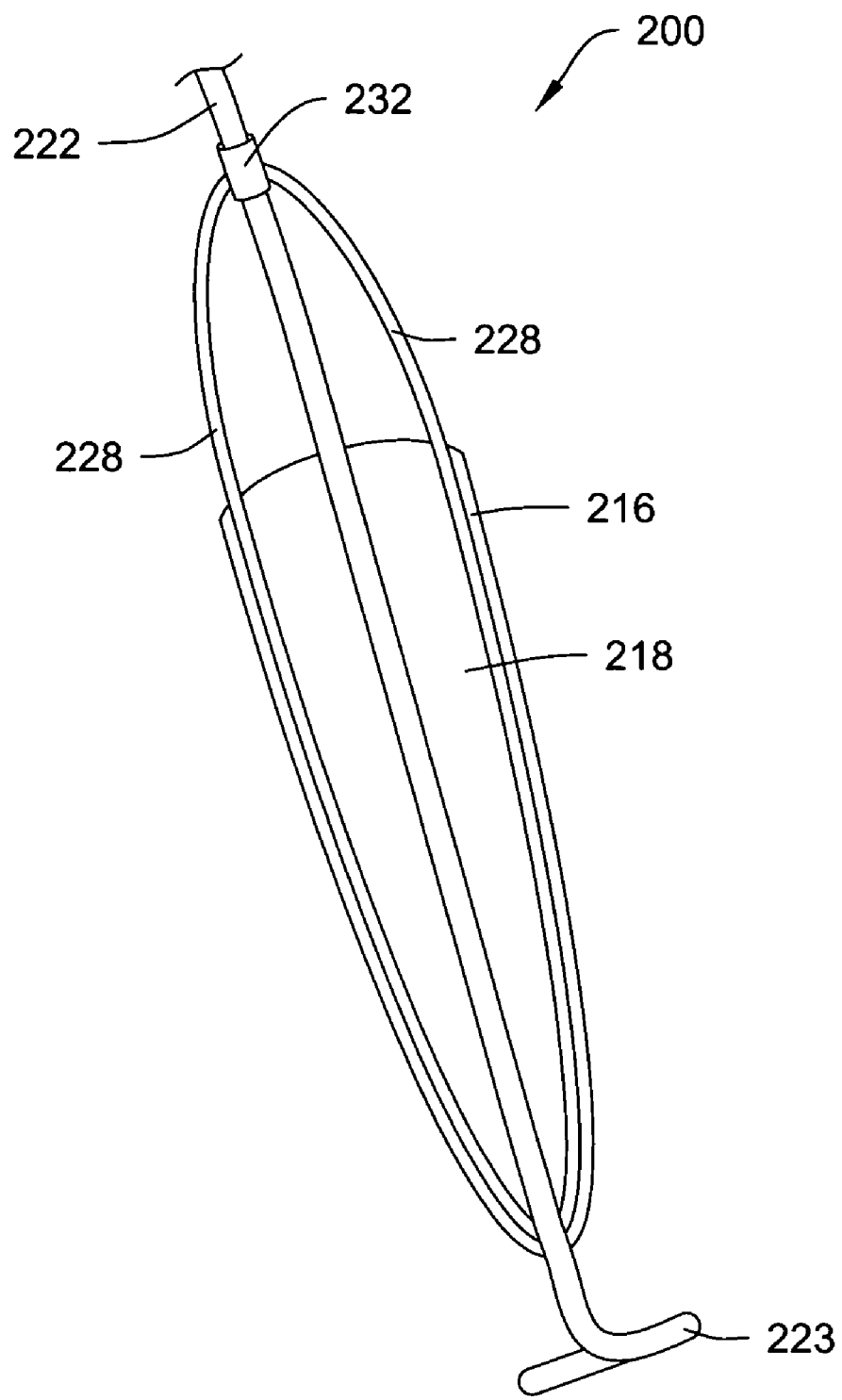
FIG. 5A depicts a diagrammatic cross-sectional view of pump 200 in a first contracted position.

FIG. 5A is a diagrammatic cross-sectional view of pump 200 according to a first embodiment. In this embodiment, when the pump moves between the expanded and the contracted position, actuation struts 228 move between the elongated position shown in this Figure and the expanded position shown in FIG. 4. The struts may be in their martensitic phase when elongated and in their austenitic phase when expanded. Alternatively, the struts may be in their austenitic phase when elongated and in their martensitic phase when expanded. A third alternative may be a configuration similar to the third alternative described above with respect to FIG. 2, where there are two sets of struts.

Figure 5B:
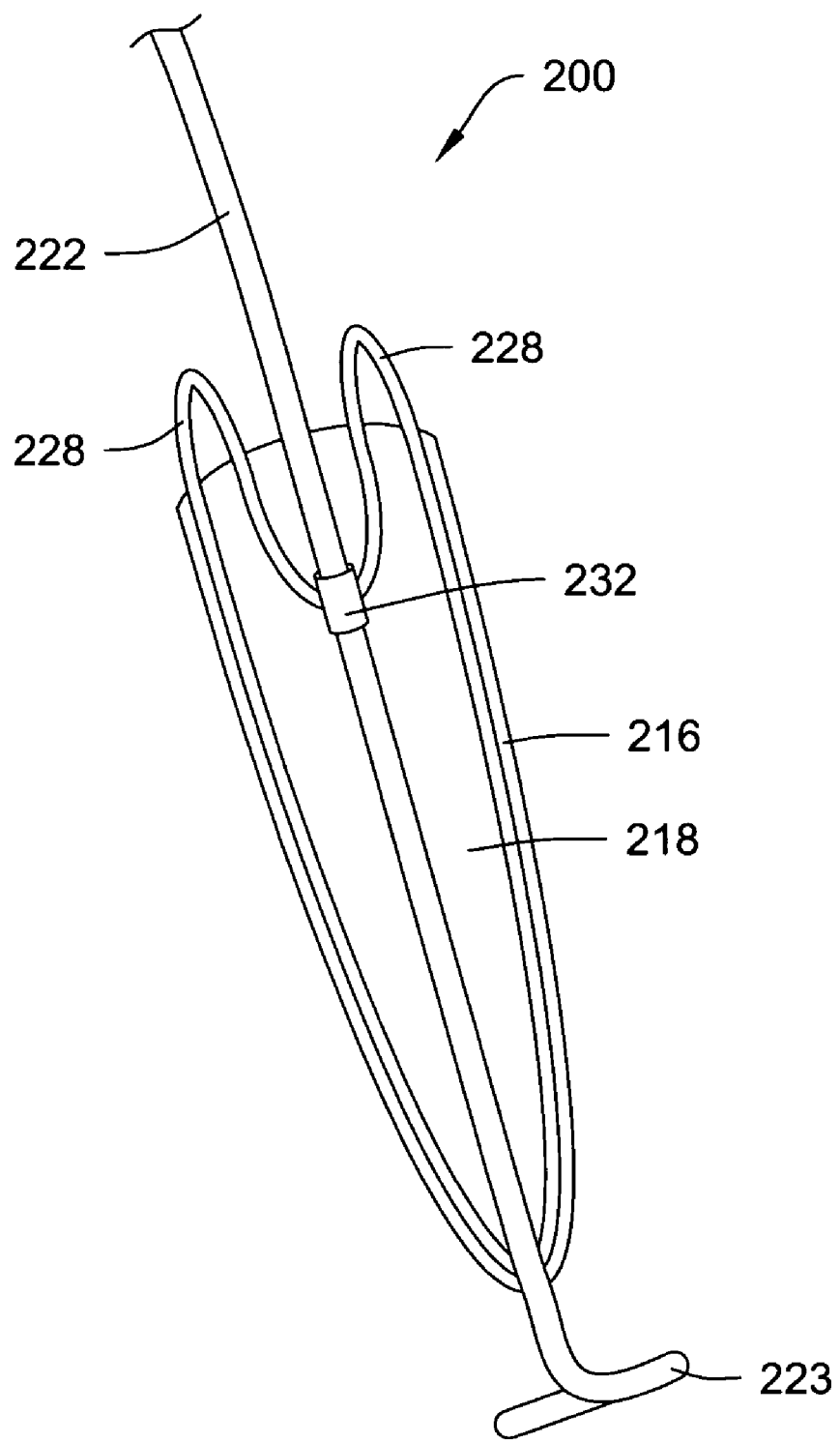
FIG. 5B depicts a diagrammatic cross-sectional view of pump 200 in a second contracted position.

FIG. 5B is a diagrammatic cross-sectional view of pump 200 according to a second embodiment. The embodiment of FIG. 5B is similar to that of FIG. 5A, except that the struts are folding inwards when the pump is in the contracted position. This may be advantageous to get the mouth of the pump closer to the aortic valve. Other configurations besides those shown are possible.

Figure 6:
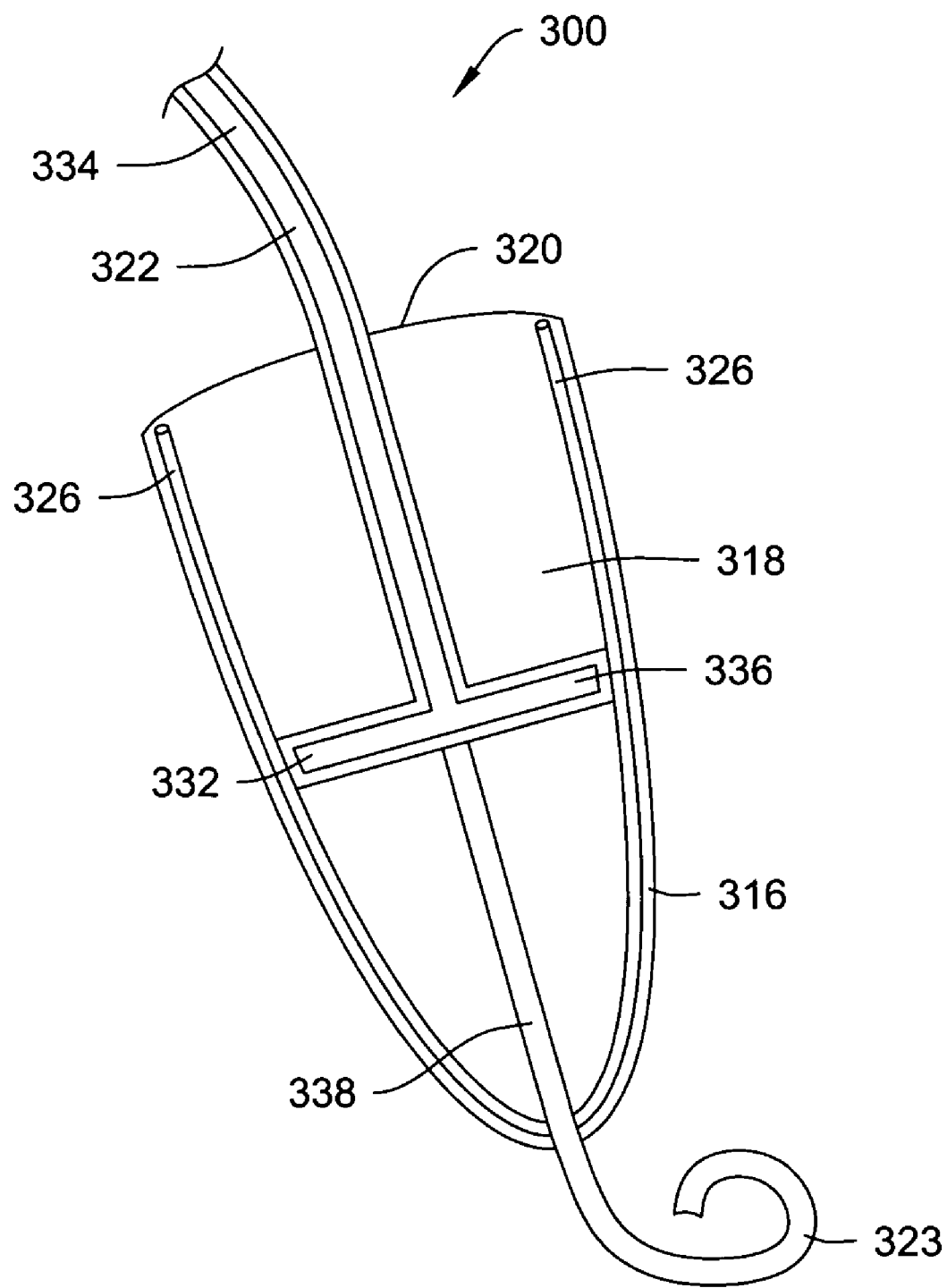
FIG. 6 depicts a diagrammatic cross-sectional view of pump 300 in an expanded position.

FIG. 6 is a diagrammatic cross-sectional view of a pump 300 shown in the expanded position. Pump 300 includes support struts 326, which may be biased to be in the contracted position. Elongate member 322 includes a first portion 334 that is fluidly connected to balloons 336, and may optionally include a second portion 338 extending to an atraumatic tail 323. Wall 316 forms pumping chamber 318, which has an opening 320, and are attached to support struts 326. When inflated, balloons 336 extend outward generally radially from the centerline of the pump and push supporting struts 326 to the expanded position. There may be any suitable number of balloon 336. Other configurations are contemplated. For example, first portion 334 could be connected to an inflatable toroidal balloon, which would function much as balloons 336 do. In operation, inflation of balloons 336 moves the pump to an expanded position. Deflation of balloons 336, which may be biased to move inwardly to the centerline, moves the pump to a contracted position, expelling the blood towards the aortic valve.

Figure 7:
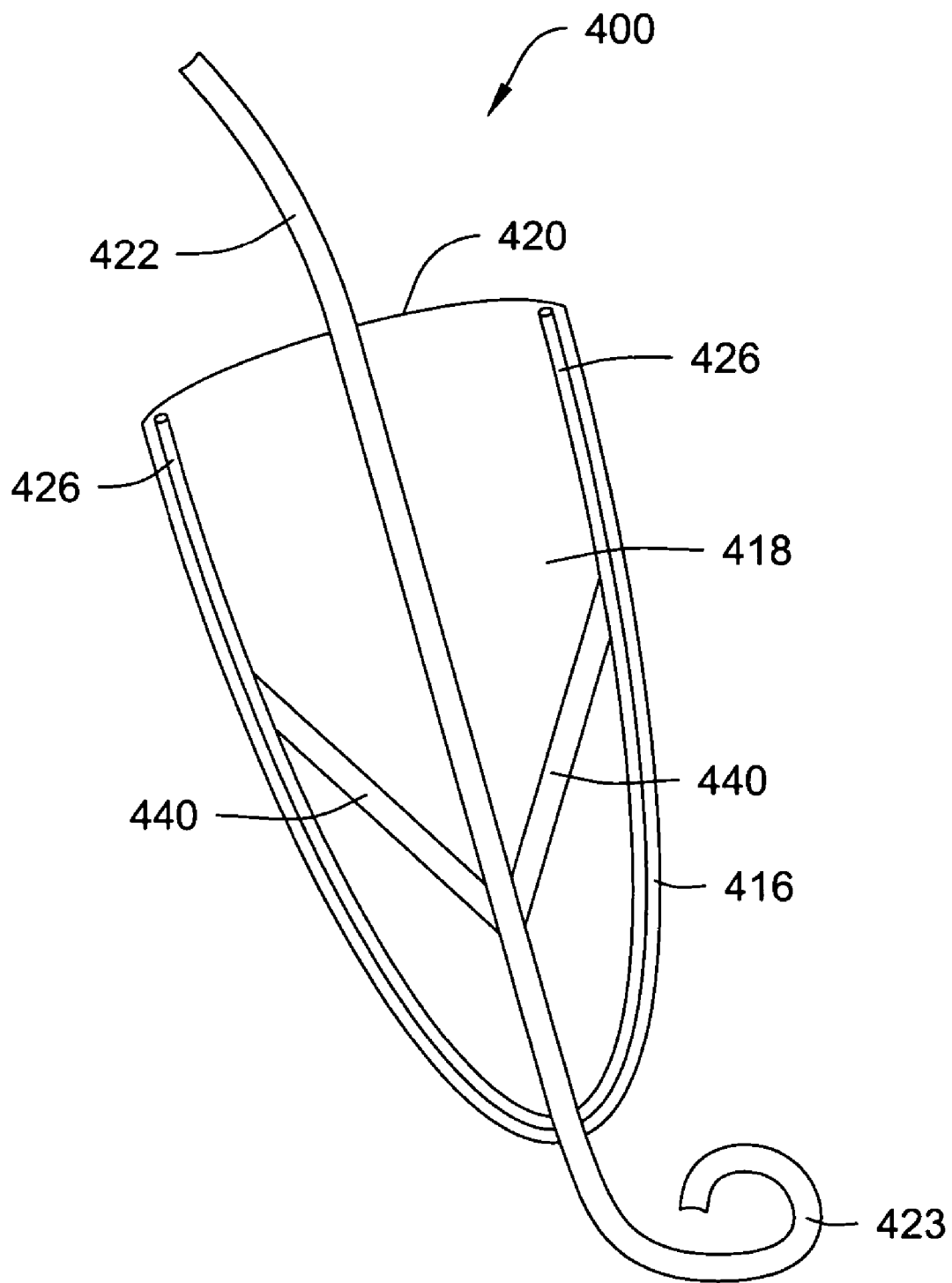
FIG. 7 depicts a diagrammatic cross-sectional view of pump 400 in an expanded position.

FIG. 7 is a diagrammatic cross-sectional view of a pump 400, which is depicted in its expanded position. Pump 400 includes a wall 416, which defines pumping chamber 418 having opening 420. Wall 416 is attached to support struts 426. Support struts 426 are attached to elongate member 422 and are generally rigid. Elongate member 422 may include atraumatic end 423, which serves to position the pump in the left ventricle. Electroactive polymer actuators 440 are attached between elongate member 422 and support struts 426. When exposed to a voltage source, actuators 440 will decrease in length; and when the exposure ceases, actuators 440 will return to their original length. The voltage path may be through elongate member 422, up electroactive polymer actuators 440, through struts 426, and back to a second electrical conduit in elongate member 422. Thus, this pump may be operated by exposing actuators 440 intermittently to a voltage source. Elongate member 422, actuators 440, and struts 426 may be electrically insulated using a suitable polymer or combination of polymers.

Electoactive polymers (EAPs) are polymers that respond to electrical stimulation by displaying size or shape displacement. For example, some electroactive polymers contract when electrically stimulated. Suitable EAPs may include ferroelectric polymers such as poly(vinylidene fluoride) and its copolymers, acrylic elastomer tape such as VHB™ sold by 3m™, electrostrictive graft elastomers such as an elastomer grafted to a piezoelectric poly(vinylidene fluoride-trifluoro-ethylene) copolymer, and liquid crystal elastomer materials such as monodomain nematic liquid crystal elastomers with conductive polymers distributed within their network structure. Other EAPs that may be suitable in this application include ionic EAPs such as ionic polymer gels such as polyacrylonitrile materials, ionomeric polymer-metal composites, conductive polymers such as those frabricated from polypyrrole, polyaniline, PAN doped with HCl, polyethylenedioxythiophene, poly(p-phenylene vinylene)s, or polythiophenes, and carbon nanotubes.

Figure 8:
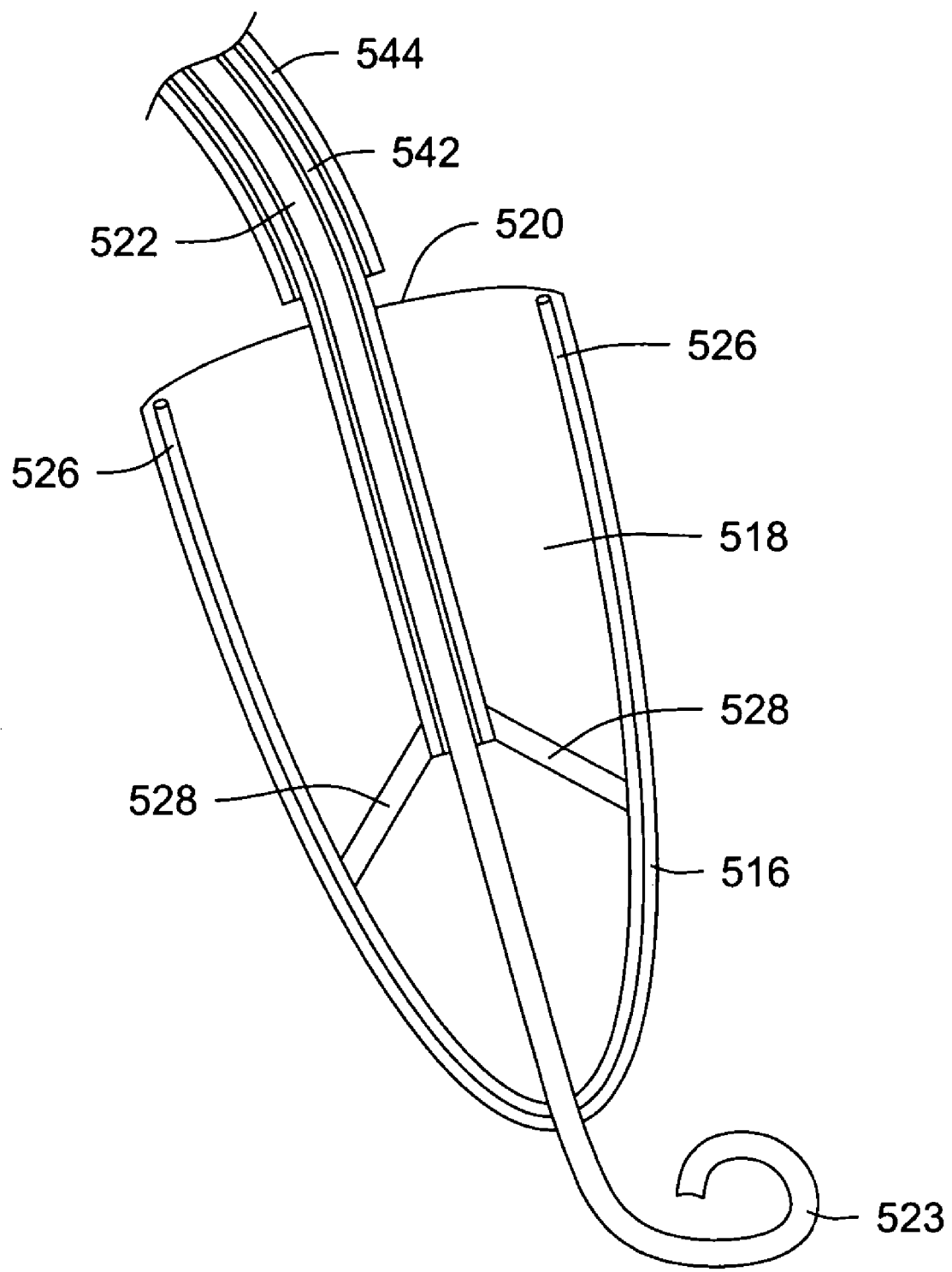
FIG. 8 depicts a diagrammatic cross-sectional view of pump 500 in an expanded position.

FIG. 8 is a diagrammatic cross-sectional view of a pump 500. Pump 500 includes wall 516, which forms pumping cavity 518 having opening 520. An elongate member 522 passes through the center of pumping cavity 518 and may include atraumatic end 523, which may be a flexible coil or other suitable configuration. Wall 516 is attached to support struts 526, which are attached at one end to elongate member 522. The actuation mechanism consists of actuating struts 228. Actuating struts 228 are attached at one end to support struts 526 and at the other end are attached to sliding member 542. Sliding member 542 is disposed over elongate member 522 and is configured to easily slide proximally and distally with respect to elongate member 522. A sheath 544 may be disposed over sliding member 542. Struts 528 may be made from a relatively rigid material. There may be any suitable number of actuating and support struts. For example, there may be 3, 4, 5, 6 , 7, or 8 actuating struts. In use, movement of sliding member 542 proximally and distally moves actuating struts 528 inward and outward, which in turn moves support struts 526 inward and outward. This movement expands and contracts the pump wall, thereby pumping the fluid.

Each of these pumps would be attached to a power source, which would provide electrical power or pressurized fluid. The power source may include a control mechanism to control the rate of operation of the pump. The control mechanism may be configured to receive data from a heart monitoring device or a pacemaker to synchronize the operation of the pump with the operation of the left ventricle. Each pump may also be coated with an anti-clotting agent or other suitable therapeutic agent.

It should be understood that this disclosure is, in many respects, only illustrative. Numerous advantages of the invention covered by this document have been set forth in the foregoing description. Changes may be made in details, particularly in matters of shape, size and arrangement of parts without exceeding the scope of the invention. Those of skill in the art will readily appreciate that other embodiments may be made and used which fall within the scope of the claims attached hereto. The invention's scope is, of course, defined in the language in which the appended claims are expressed.

What is claimed is:

1. A medical device, for use in a patient's vasculature comprising
    a blood-impermeable wall defining a cavity having a lumen through the wall at a first end opposite a second end, the wall including a flexible section;
    a frame attached to the wall;
    an elongate member attached to the frame and extending through the cavity; and
    an actuation system comprising one or more actuating members, the one or more actuating members connecting the frame to the elongate member, the actuation system configured to move the frame between an expanded position and a contracted position.

2. The medical device of claim 1, wherein the actuation system comprises a shape memory material having a transformation temperature and means for moving the shape memory material through its transformation temperature.

3. The medical device of claim 1, wherein the one or more actuating members comprise struts formed of a shape memory material, and wherein the struts are electrically connected to a voltage source.

4. The medical device of claim 1, wherein the actuation system comprises an electroactive polymer.

5. The medical device of claim 1, wherein a cross-section of the cavity at the first end is larger than a cross-section of the cavity at the second end when the frame is in the expanded position.

6. The medical device of claim 5, wherein the cavity has a generally conical shape when the frame is in the expanded position.

7. The medical device of claim 5, wherein the cavity has a slightly flattened conical shape when the frame is in the contracted position.

8. A medical device, for use in a patient's vasculature comprising
    a blood-impermeable wall defining a cavity having a lumen through the wall at a first end opposite a second end, the wall including a flexible section;
    a frame attached to the wall;
    an elongate member attached to the frame and extending through the cavity; and
    an actuation system comprising one or more actuating members, the one or more actuating members connecting the frame to the elongate member, the actuation system configured to move the frame between an expanded position and a contracted position;
    wherein the actuation system comprises a balloon and an inflation lumen fluidly attached to the balloon.

9. A medical device, for use in a patient's vasculature comprising a blood-impermeable wall defining a cavity having a lumen through the wall at a first end opposite a second end, the wall including a flexible section;

a frame attached to the wall;

an elongate member attached to the frame and extending through the cavity; and an actuation system comprising one or more actuating members, the one or more actuating members connecting the frame to the elongate member, the actuation system configured to move the frame between an expanded position and a contracted position;

wherein the cavity has a volume of between 40 cc and 100 cc.

10. The medical device of claim 9, wherein the cavity has a volume of between 60 cc and 85 cc.

11. A medical device, for use in a patient's vasculature comprising a blood-impermeable wall defining a cavity having a lumen through the wall at a first end opposite a second end, the wall including a flexible section;

a frame attached to the wall;

an elongate member attached to the frame and extending through the cavity; and an actuation system comprising one or more actuating members, the one or more actuating members connecting the frame to the elongate member, the actuation system configured to move the frame between an expanded position and a contracted position;

the medical device further comprising an anti-clotting agent.

12. An intravascular pump, comprising:

a flexible wall defining a pumping chamber; and a pumping mechanism including a frame attached to the wall wherein the pumping mechanism comprises: an elongate member attached to the frame and extending through the chamber; and an actuation system comprising one or more actuating members, the one or more actuating members connecting the frame to the elongate member, the actuation system configured to move the frame between an expanded position and a contracted position.

13. The pump of claim 12, wherein the pumping mechanism includes a central shaft and moveable struts extending between the central shaft and the frame.

14. The pump of claim 13, wherein the pumping mechanism includes a balloon.

15. The pump of claim 13, wherein the pumping mechanism further includes a member made from a shape memory alloy having a transformation temperature and means to move the shape memory alloy through the transformation temperature.

16. The pump of claim 15, wherein the shape memory alloy comprises Nitinol.

17. The pump of claim 13, wherein the pumping mechanism further includes an electroactive polymer.

18. The pump of claim 13, further comprising a control system for controlling the pump.

19. The pump of claim 18, wherein the control system comprises a sensor for measuring heart activity.

20. The pump of claim 18, wherein the control system includes an interface for use with a pacemaker.

* * * * *